United States Patent
Banjanin et al.

(10) Patent No.: US 11,779,311 B2
(45) Date of Patent: Oct. 10, 2023

(54) METHOD AND APPARATUS FOR PERFORMING SPECTRAL DOPPLER IMAGING

(71) Applicant: FUJIFILM SonoSite, Inc., Bothell, WA (US)

(72) Inventors: Zoran Banjanin, Bellevue, WA (US); Andrew Lundberg, Woodinville, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 622 days.

(21) Appl. No.: 16/132,237

(22) Filed: Sep. 14, 2018

(65) Prior Publication Data

US 2020/0085410 A1    Mar. 19, 2020

(51) Int. Cl.
- *A61B 8/08* (2006.01)
- *A61B 8/02* (2006.01)
- *A61B 5/08* (2006.01)
- *A61B 5/0245* (2006.01)

(52) U.S. Cl.
CPC ............ *A61B 8/488* (2013.01); *A61B 5/0245* (2013.01); *A61B 5/0816* (2013.01); *A61B 8/02* (2013.01); *A61B 8/5207* (2013.01); *A61B 8/5223* (2013.01)

(58) Field of Classification Search
CPC ......... A61B 8/488; A61B 8/02; A61B 8/5207; A61B 8/5223; A61B 5/0245; A61B 5/0816
See application file for complete search history.

(56) References Cited

U.S. PATENT DOCUMENTS

| | | |
|---|---|---|
| 5,476,097 A | 12/1995 | Robinson |
| 2005/0251040 A1* | 11/2005 | Relkuntwar ........... A61B 8/565 600/437 |
| 2006/0293595 A1 | 12/2006 | Clark et al. |
| 2007/0043294 A1 | 2/2007 | Li |
| 2009/0012398 A1* | 1/2009 | Zhang ................ G01S 15/8979 600/453 |
| 2012/0215110 A1* | 8/2012 | Wilkening ............ G01S 7/5209 600/453 |
| 2012/0316444 A1 | 12/2012 | Shim et al. |
| 2013/0261429 A1* | 10/2013 | Lee ...................... A61B 5/0035 600/411 |

(Continued)

OTHER PUBLICATIONS

International Search Report and Written Opinion for Application No. PCT/US2019/050664, dated Dec. 26, 2019, 13 pages.

(Continued)

*Primary Examiner* — John Denny Li (74) *Attorney, Agent, or Firm* — Womble Bond Dickinson (US) LLP (57) ABSTRACT

An ultrasound imaging system performs spectral Doppler processing in a manner that considers a physiological cycle of a subject. In one embodiment, gaps in a spectral Doppler signal are filled taking by a processor that analyzes changes in the spectral Doppler signal caused by a physiological cycle. Spectral Doppler data are scaled to fit with the data occurring before and after a gap. The firing order of an interleaved imaging mode can also be adjusted so that spectral Doppler imaging is not interrupted during predefined or user defined portions of a physiological cycle.

15 Claims, 6 Drawing Sheets

(56) References Cited

U.S. PATENT DOCUMENTS

| 2014/0018683 A1* | 1/2014 | Park | A61B 8/5207 |
| | | | 600/453 |
| 2017/0143311 A1* | 5/2017 | Srinivasan | A61B 8/0891 |
| 2020/0182989 A1* | 6/2020 | Freeman | G01S 7/52095 |

OTHER PUBLICATIONS

International Preliminary Report and Written Opinion on the Patentability of Application No. PCT/US2019/050664 dated Mar. 25, 2021, 10 pages.
Extended European Search Report on the Patentability of Application No. 19860535.4 dated May 3, 2022, 8 pages.

* cited by examiner

METHOD AND APPARATUS FOR PERFORMING SPECTRAL DOPPLER IMAGING

TECHNICAL FIELD

The technology disclosed herein relates to ultrasound imaging and to spectral Doppler imaging in particular.

BACKGROUND

Figure 1:
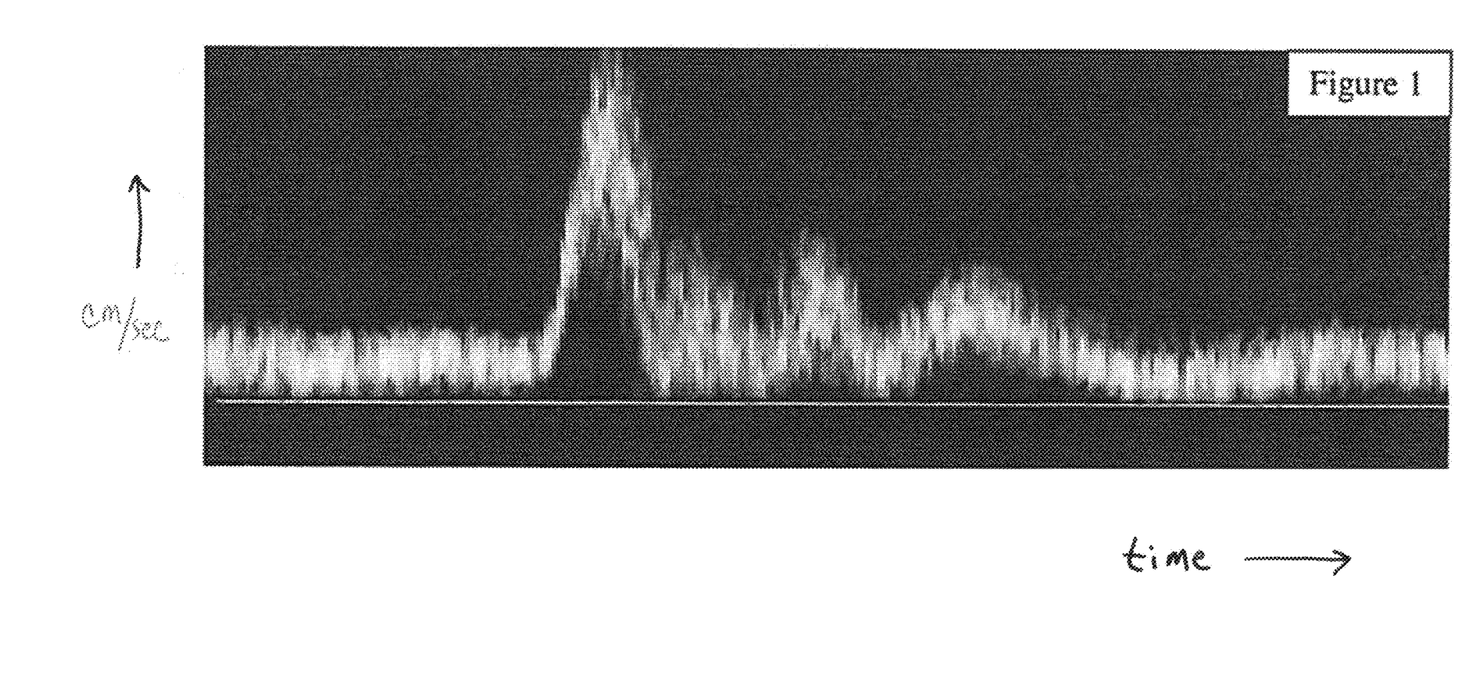
FIG. 1 shows a conventional continuous spectral Doppler signal.

Spectral Doppler is an imaging mode that provides useful information about cardiac and vessel health to physicians and health care providers. With conventional Doppler processing, ultrasound signals are directed into a region of interest and the Doppler shifts caused by reflections from moving tissue or blood flow are detected. Spectral Doppler processing performs an extra step of analyzing the frequency content of the detected Doppler signals. FIG. 1 illustrates a typical Spectral Doppler signal. The horizontal axis represents time and the vertical axis represents the frequencies present in the detected Doppler signals at any point in time. The Doppler frequency is most often shown as a velocity (e.g. cm./sec) by taking into account the transmit carrier frequency, speed of sound and the propagation direction.

During the systolic phase of the cardiac cycle (i.e. when the heart is contracting to eject blood), there is a large spike in the detected velocity of the moving blood. During the diastolic phase of the cardiac cycle (when the heart is filling with blood), the velocity of the moving blood is much lower. How the velocity changes with the cardiac cycle can be indicative of disease or other physiological conditions.

Figure 2:
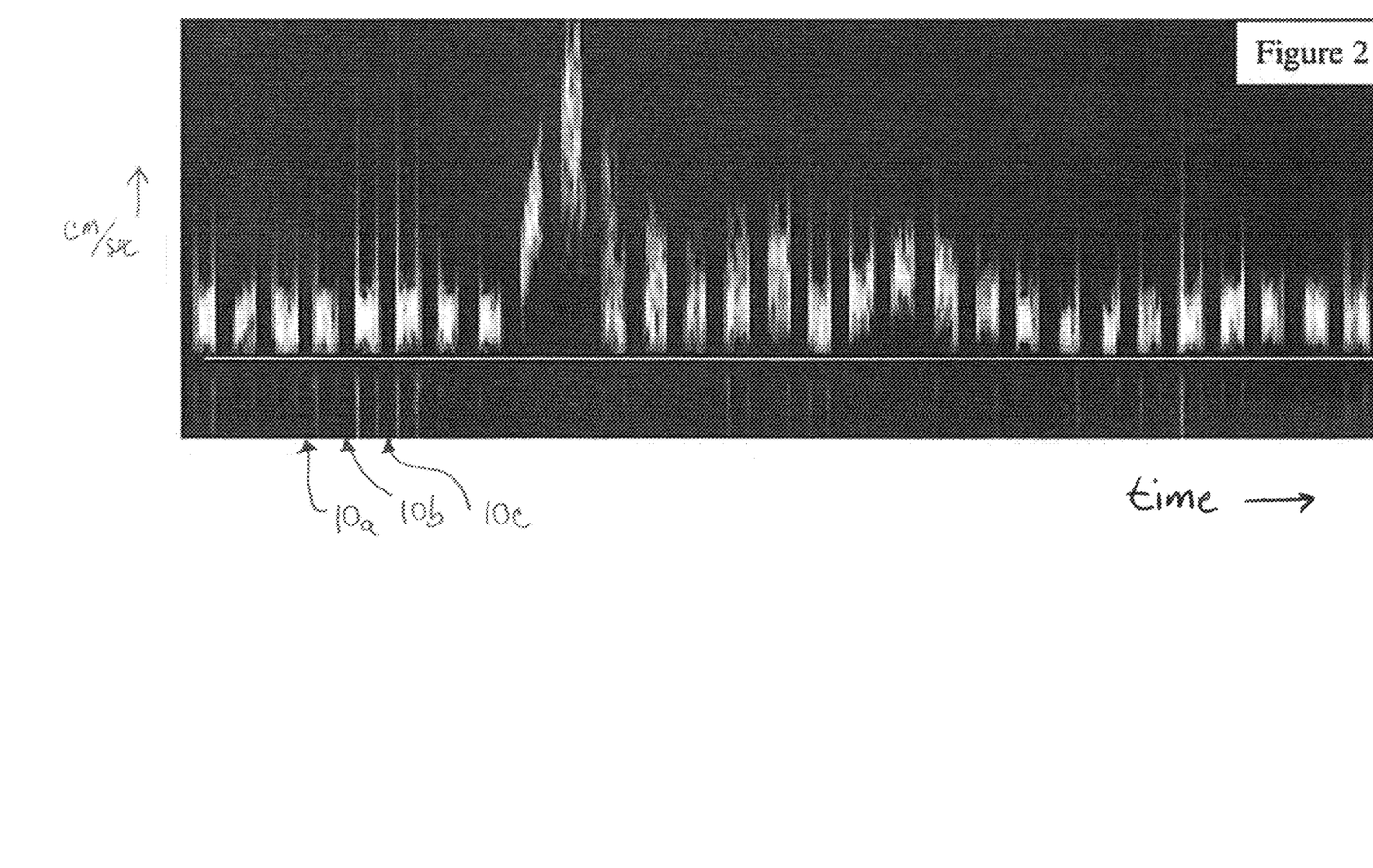
FIG. 2 shows a spectral Doppler signal with gaps caused by an interleaved imaging mode.

To perform a spectral Doppler mode examination, a user manipulates an ultrasound probe to direct ultrasound energy at a desired region of interest. The user then sets a control on the ultrasound imaging machine to adjust the depth of a range gate that defines a small subset of the region of interest in which the Doppler shifts of the returned echo signals are to be measured. To obtain consistent results over multiple cardiac cycles, the range gate should remain in the same location. If the user accidently moves the probe, then the spectral Doppler signals will change. To help keep the probe in the desired orientation, many ultrasound imaging systems interleave one or more other modes with spectral Doppler processing. For example, B-mode imaging can be interleaved with spectral Doppler processing by firing ultrasound signals on a number of beamlines to insonify an entire region of interest followed by Doppler firings on the beamline for the range gate and then firing another set of B-mode imaging signals and so forth. The B-mode images of the region of interest are displayed on a video monitor so that the user can see if the range gate is in the desired location. Under some conditions, the interleaving causes the spectral Doppler signal to have gaps 10a, 10b, 10c etc. when no Doppler signals are detected while the imaging system is performing B-mode imaging as shown in FIG. 2. The gaps in the spectral Doppler signal contain no useful information and may occur at times when the physician would like to see the signal.

Figure 3:
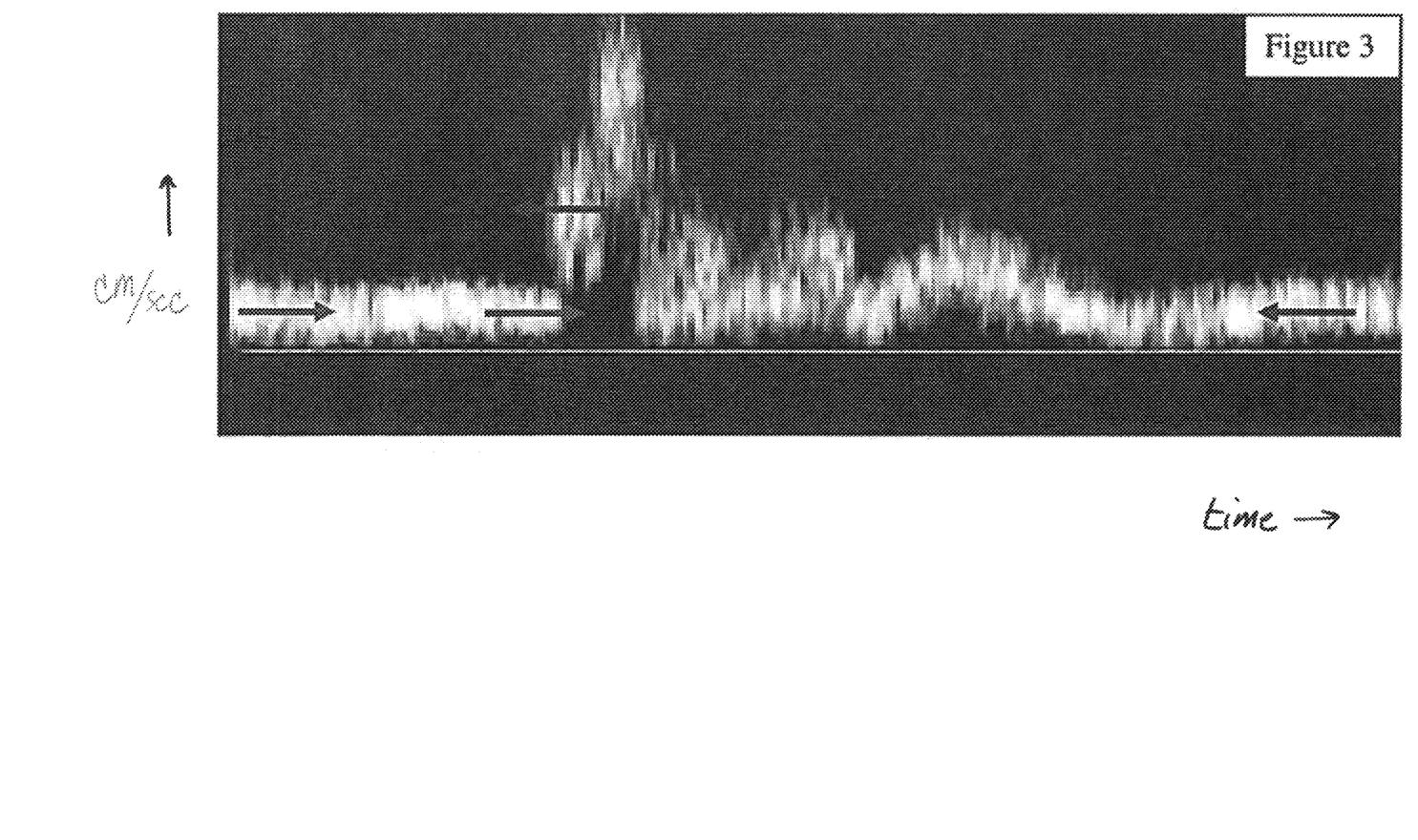
FIG. 3 shows a known technique for filling gaps in a spectral Doppler signal with spectral Doppler data from an area that is adjacent to a gap.

There are known techniques to fill in the gapped portions of the spectral Doppler signal by copying adjacent Doppler data and pasting it into the gaps of an interleaved Doppler signal as proposed by Robinson U.S. Pat. No. 5,476,097 There are other approaches that perform moving average (MA) modeling (Kristoffersen, U.S. Pat. No. 4,559,952) or auto regressive (AR) modeling (Wang, U.S. Pat. No. 5,642,732) of adjacent Doppler data. These models are used to generate "clones" of adjacent Doppler data to fill the gaps. FIG. 3 shows an example of such a gap filling technique, whereby a portion of the Doppler signals to the left or right of a gap are copied or cloned into the gap. Previous techniques suggest that left and right copies or clones overlap and blend in middle of the gap to make the Doppler signal smoother. While this approach can make the spectral Doppler signal look smoother when the signal is not changing rapidly, such an approach does not work well for gaps that are near portions of the signal where large changes are occurring.

Given these problems, there is a need for a better way to perform spectral Doppler imaging.

SUMMARY

To address the above-described problems, the disclosed technology relates to an ultrasound imaging system that performs spectral Doppler processing by analyzing the physiology of the subject. In one embodiment, data that are used to fill in a gap in an interleaved spectral Doppler signal are scaled or adjusted based upon where the gap is in a physiological cycle. In one embodiment, a mean frequency of the segments of the spectral Doppler signals occurring before and after a gap are determined and used to modify copies or clones of adjacent spectral Doppler data that will fill a gap. In one embodiment, the mean frequencies of the spectral data before and/or after the gap are used to shift the mean frequency of copies or clones of adjacent Doppler data to produce a spectral Doppler signal with a mean frequency that fits between the mean frequencies of the adjacent portions of the spectral Doppler signal.

In one embodiment, the system performs spectral Doppler processing during one or more predefined times during a subject's physiological cycle. In one embodiment, spectral Doppler processing is not interrupted at the peak systole or at the end of the diastole portion of a cardiac cycle. A processor estimates when events will occur in the subject's cardiac cycle and modifies the firing order of the spectral Doppler processing versus other imaging modes so that the other imaging modes are not used during pre-defined or user selected points in the cardiac cycle.

In one embodiment, a display of a spectral Doppler signal on a video monitor is triggered based on a threshold in the spectral Doppler signal or from a signal received from an external sensor. With the trigger threshold defined, the displayed spectral Doppler signal appears stationary on the video monitor.

In another embodiment, a processor in an ultrasound imaging system records and stores a length of spectral Doppler data that includes a predefined number of physiological cycles. Studies performed at different times can always include the same number of cycles and can therefore be more easily compared. In addition, derived waveforms (e.g., peak, mean waveforms etc.) can be more easily compared from different studies.

DETAILED DESCRIPTION

As indicated above, the described technology relates to improvements in a spectral Doppler (Pulse wave (PW) or Continuous wave (CW)) imaging mode used in ultrasound imaging systems. In one embodiment, gaps in a Doppler signal that are caused by an interleaved imaging mode are filled with actual or cloned Doppler data that are adjusted in accordance with a subject's physiology (e.g. cardiac cycle). In one embodiment, Doppler data are copied from an area prior to or after a gap and mixed (e.g. scaled in frequency) so that a mean frequency of the copied or cloned data fits between the mean frequencies of the Doppler data before and after the gap.

Figure 4A:
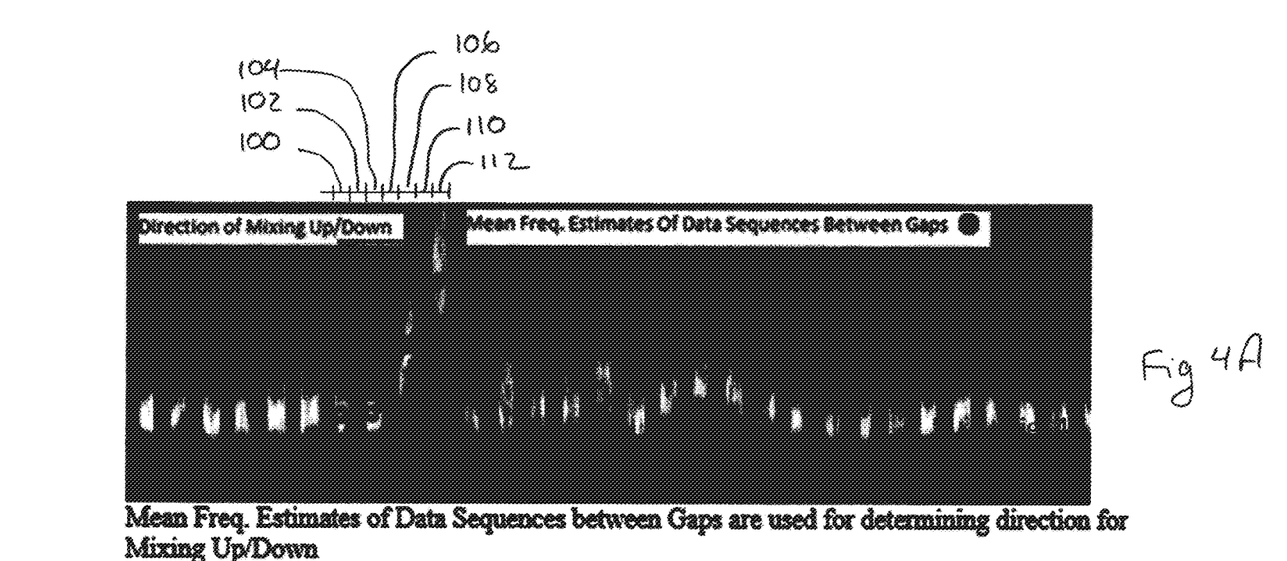
FIGS. 4A and 4B show one technique for filling gaps in a spectral Doppler signal in accordance with an embodiment of the disclosed technology.
Figure 4B:
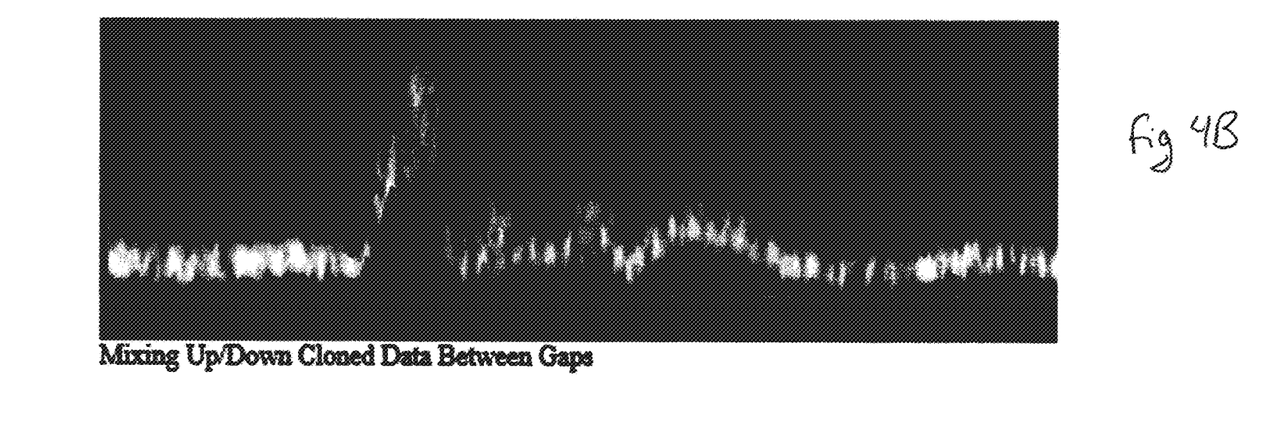

FIG. 4A illustrates a spectral Doppler signal recorded over a single cardiac cycle of a subject. The spectral Doppler signal includes sections of Doppler data that are separated by a number of gaps. In the illustration, two Doppler data sections 100, 104 are recorded at the end of the diastole phase of the cardiac cycle. A Doppler data section 108 is recorded midway on the rise to the peak of the systole phase of the cardiac cycle and a Doppler data section 112 is recorded at the peak of the systole phase. A gap 106 occurs early during the systole phase while a gap 110 occurs just before the peak of the systole phase.

To fill in the gaps (for example gaps 106, 110), a processor analyzes one or more sections of Doppler data before and/or after the gaps. Doppler data to fill the gaps are scaled based on the analysis and used to fill the gap. In one embodiment, a processor determines the mean frequency of the Doppler data for a number of recorded sections, such as sections 100, 104, 108 and 112, and determines how to create the data that are to be used to fill the gaps.

In one embodiment, Doppler data adjacent to a gap (or nearly adjacent such as within one to three gaps) are copied or cloned and mixed/scaled. Which side of the gap that the data are taken from can also be determined from the analysis of the recorded Doppler data. In the example shown, there are gaps 106, 110 occurring in the systole portion of the cardiac cycle before the peak is reached at 112 and one set of actual Doppler data 108 recorded midway to the peak. In one embodiment, the Doppler data 108 are scaled both up and down in frequency so that the mean frequency of the scaled data fits between the mean frequencies of the adjacent actual Doppler data and are copied to fill in the gaps 106 and 110.

In one embodiment, the copied Doppler data are scaled in the time domain by mixing the data (e.g. by multiplying the data by a sinusoid with a different mean frequency). For example, if the mean frequency of the Doppler data 108 is 1500 Hz and the mean frequency of the Doppler data 112 at the peak systole is 2000 Hz., then a copy of the Doppler data 108 can be mixed upwards so that the data have a mean frequency that changes to 1750 Hz and used to fill the gap 110. Similarly, if the mean frequency of the Doppler data 104 is 1000 Hz, then a copy of the Doppler data 108 can be mixed downwards to have a mean frequency of 1250 Hz and used to fill the gap 106. The mixing frequency need not be constant. In some embodiments, the mixing frequency is not constant and can be determined by the frequencies of the actual Doppler data that adjoin the ends of the gaps. In this manner, the copied data fit smoothly with the actual data and avoids any frequency discontinuities.

In one embodiment received Doppler data having a mean frequency between the mean frequencies of its neighbors are selected and scaled to fill a gap (e.g. Doppler data 108 have a mean frequency between the mean frequencies of Doppler data sections 104 and 112 are used to fill the gaps 106 and 110). In another embodiment, Doppler data occurring prior to a gap could be used or Doppler data after a gap could be used.

The disclosed technology is not limited to only using one mean frequency. In some embodiments, multiple mean frequencies could be calculated from subsections of adjacent Doppler data such as the mean frequency for every 5 microseconds. Calculating multiple mean frequencies from subsections of adjacent Doppler data could be utilized to predict Doppler data trends and thus, scale the Doppler data more accurately. In some embodiments, additional mean frequencies from Doppler data in other than the two adjacent sections (sections 100, 112 of FIG. 4A) of Doppler data can be used to fill a gap 106. In some embodiments, utilizing additional mean frequencies from additional sections can be used to predict where the gaps are occurring in the cardiac cycle, such as if the gaps fall at the peak of the systole or at the bottom of diastole.

In some embodiments, the gaps are not filled with copied or cloned Doppler data. Instead pre-fast Fourier transformed (FFT) echo data are generated such that the FFT of the generated echo data will have a signal characteristic required to smoothly fill in a gap. For example, when the data are scaled based on the mean frequency of the Doppler data adjacent a gap, pre-FFT echo data are generated so that the mean frequency of the FFT of the generated echo data will have the desired mean frequency.

In some embodiments, in order to generate the pre-FFT echo data, an inverse FFT can be used, such as x(t)=IFFT(X(f)), where X(f) is the desired Doppler data in frequency domain.

Once the synthetic pre-FFT echo data are generated, they are added to the actual recorded echo data and then analyzed in the frequency domain to produce a continuous spectral Doppler signal. In one embodiment, spectral Doppler data are copied and mixed to the desired frequency. The inverse FFT of the spectral Doppler signal is calculated by a processor and the synthesized pre-FFT data are combined with received pre-FFT data at the time of the gaps and processed together to produce a spectral Doppler signal with no gaps.

Although the disclosed embodiments scale Doppler data to be copied into a gap based on the detected mean frequencies of the Doppler data adjacent a gap, it will be appreciated that other measurements of the spectral Doppler signal could be used such as the median frequency, peak frequency, minimum frequency, variance in frequency etc. Also, it is not necessary that the scaling be linear (e.g. half-way between its neighbors) to fill a gap. Scaling can be performed such that a plot of the frequency measurements, or other parameter used for scaling, will smoothly follow the cardiac or other physiological cycle. Such scaling could be by splines etc. to achieve a smooth curve.

In another embodiment of the disclosed technology, the firing order of ultrasound system is altered so that spectral Doppler imaging is not interrupted during one or more desired time periods in a physiological cycle. Many clinicians are interested in the characteristics of the spectral Doppler signal at the end of the diastole and at the peak of the systole portions of a cardiac cycle. In some embodiments, in order to ensure that actual rather than synthesized spectral Doppler signal data are obtained during these times, a processor in the ultrasound imaging system can change the firing order of the transmitted signals of the ultrasound imaging system operating in an interleaved firing mode so that spectral Doppler imaging is not interrupted during these times.

Figure 5:
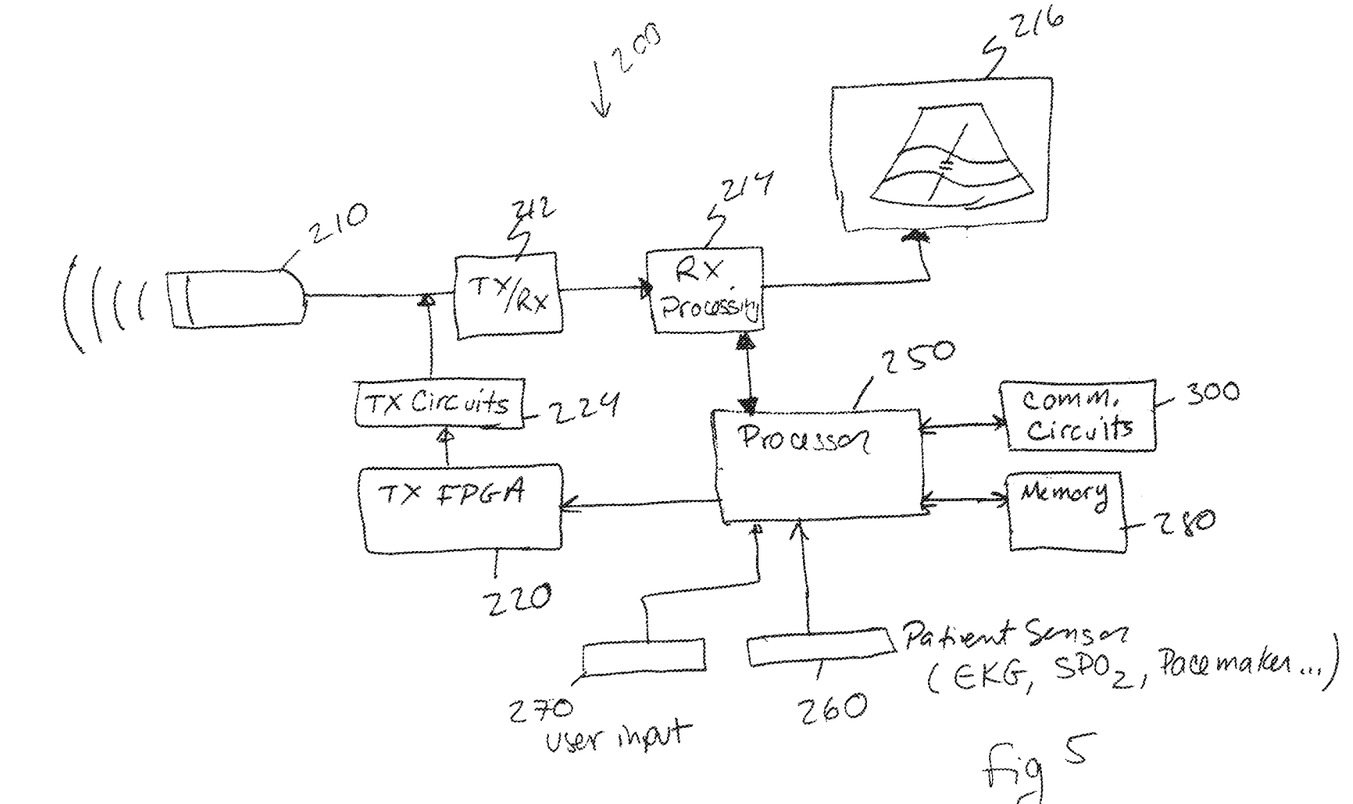
FIG. 5 is a block diagram of an ultrasound imaging system that adjusts a firing order of ultrasound imaging signals in accordance with a subject's detected or predicted physiological cycle in accordance with an embodiment of the disclosed technology.

FIG. 5 shows a simplified block diagram of an ultrasound imaging system that includes a processor or programmed logic that is configured to modify a firing order of transmitted ultrasound signals such that spectral Doppler imaging is not interrupted during one or more periods of interest. The ultrasound imaging system 200 includes an imaging transducer 210 and receive (RX) electronics 214 (e.g. amplifiers, filters, A/D converters, digital signal processors, graphics processors and the like) that process received analog echo signals and produce digital echo data for display on one or more video monitors 216. The RX electronics 214 are coupled to the transducer 210 through a transmit/receive switch 212 that is open when the transducer is directing ultrasound signals into a region of interest and closed when the RX electronics 214 are receiving the corresponding echo signals.

On the transmit side, transmit logic circuitry 220 such as a dedicated logic circuit, processor or an FPGA is configured to produce driving signals for the individual piezoelectric elements in the transducer 210. The driving signals produced depend on the type of imaging mode being used. In B-mode imaging for example, driving signals are produced that will steer transmitted ultrasound over a region of interest so that the entire region is insonified. In spectral Doppler imaging, driving signals are produced that generate ultrasound pulses along the same beam line so that the shift in frequency of the return echoes in the area of the range gate can be detected. Transmit circuitry 224 includes circuitry for boosting the voltage of the driving signals produced by the transmit logic circuitry 220 to a level that is sufficient to cause the piezoelectric elements in the transducer 210 to vibrate and generate the corresponding acoustic signals.

In one embodiment of the invention, the firing order of the driving signals produced by the transmit logic circuitry 220 is controlled by a programmed processor 250 or other logic circuit to ensure that spectral Doppler imaging is not interrupted during one or more designated times in a subject's physiological cycle. In one embodiment, the processor 250 receives signals from one or more sensors 260 connected to the subject that monitor the subject's physiological cycle. In one embodiment, the physiological cycle is the cardiac cycle and the sensor 260 is an EKG sensor, SPO$_2$ sensor, pacemaker or any other sensor capable of detecting the subject's heart beat or pulse including the Doppler ultrasound signal itself. The processor 250 is configured to execute instructions stored in a non-transitory computer readable media or that are hard coded to receive signals from the sensor 260. From the signals, the processor 250 is programmed to analyze past physiological cycles and predict the timing of when events will occur in the next physiological cycle. For example, if the heart rate is relatively steady, then the time of the next Systole phase can be determined by extrapolating from the times of the previous Systole phases. In other cases, the electrical signals (e.g. EKG signals) in the body precede the actual physical response by a sufficient time to allow the processor 250 to adjust the order of the driving signals produced by the transmit logic circuitry 220 before a particular point in the physiological cycle when the spectral Doppler imaging mode should not be interrupted. In some embodiments, the logic for predicting systole and diastole phases is based on predicted times measured from previous cycles or detected biological signals. In other embodiments, machine learning, artificial intelligence, or neural networks can be trained on historical data (e.g. sequences of EKG or respiration signals, pacemaker signals or the like) and utilized to predict systole and diastole phases of the cardiac cycle. With the predicted phases, the firing order of the ultrasound imaging system is adjusted to ensure spectral Doppler imaging during these portions of the physiological cycle.

The modification of the driving signals produced by the transmit logic circuitry 220 can be controlled by slowing the B-mode frame rate, changing the number of lines transmitted or received in a frame for B-mode imaging or changing the times when spectral Doppler mode and B-mode imaging is performed. In one embodiment, the processor 250 modifies the firing order of the driving signals produced so that the spectral Doppler imaging mode is not interrupted at the peak systole or the end of the diastole periods. In other embodiments, a user can select one or more periods using an input user control 270 (keyboard, touch screen, trackball, trackpad, voice commands, buttons, knobs etc.) that can designate one or more portions of a physiological cycle when spectral Doppler imaging should not be interrupted.

Although the physiological cycle described above is the cardiac cycle, it will be appreciated that other physiological cycles could also be used such as the respiratory cycle etc. The respiratory cycle can be monitored or detected with a respiratory senor that provides signals indicative of the cycle to the processor 250. The order/timing of the driving signals from the transmit logic 220 is adjusted so that spectral Doppler imaging is not interrupted during a predefined or user selected portion of the respiratory cycle.

In accordance with another embodiment of the disclosed technology, spectral Doppler signals are displayed on a video monitor starting at a point when the signal has a detected characteristic such a particular frequency or velocity threshold. Contemporary ultrasound systems display spectral Doppler signals at arbitrary points, which can make tracking changes in spectral Doppler hard due to a lack of synchronization between waveforms (e.g., new waveforms that overwrite a previously displayed waveform). Rather than beginning the display of the signal starting at an arbitrary time point, the processor 250 in the imaging system analyzes the signal and begins displaying the signal when a characteristic of the spectral Doppler signal (such as its mean frequency/velocity or peak frequency/velocity, power or some other attribute.) has a predefined or user selected value. This has the effect of always aligning the signal at the beginning of the sweep in relatively the same place on the horizontal axis of the display regardless of the current physiology of the subject. In another embodiment, an external sensor, such an EKG sensor, provides a measure of a detected physiological signal and a trigger is defined by an event in the received signal. For example, a QRS wave in an EKG signal defines a repeating point in a cardiac cycle that can be used to start the display of a spectral Doppler signal. In some embodiments, the display of the spectral Doppler signal can begin after a variable delay that is timed by the processor after detection of the trigger event in the sensor signal. The delay could be pre-programmed, set by a user or could be variable based on an analysis of the signal from the sensor.

Figure 6:
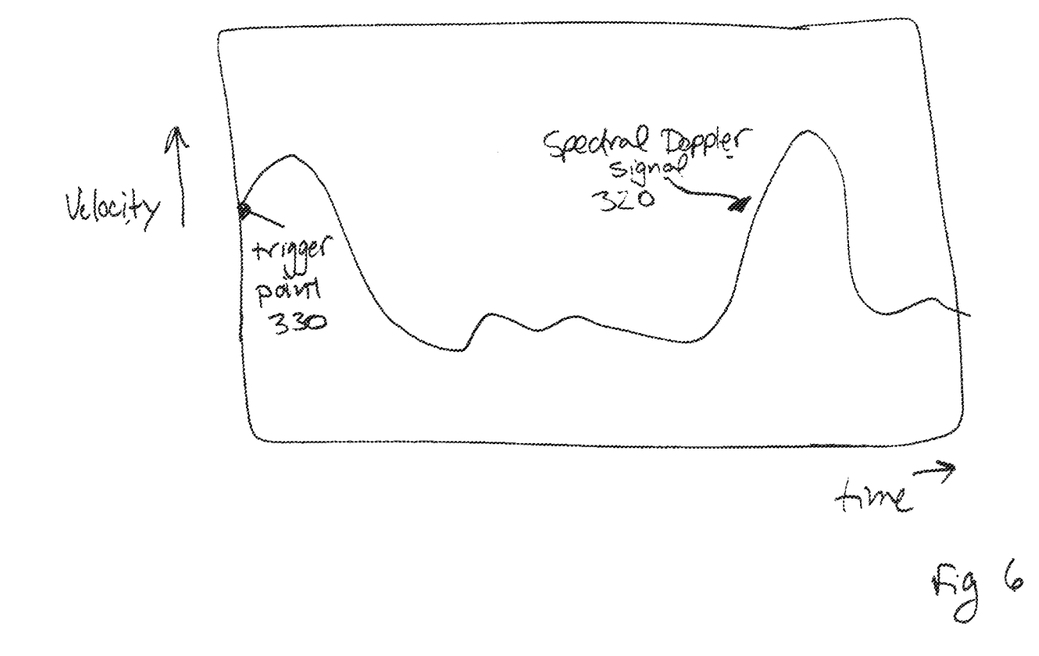
FIG. 6 is a trace of a spectral Doppler signal that is triggered on a pre-defined or user-selected value in accordance with an embodiment of the disclosed technology.

FIG. 6 illustrates a representative display of a spectral Doppler signal 320 that starts sweeping across the display when the Doppler signal meets defined criteria such as a particular peak frequency value trigger point 330. The effect is achieved in a manner similar to electrical oscilloscopes, whereby a processor analyzes a signal to locate a point where the signal meets the defined trigger criteria and begins displaying the signal from that point onwards. The signal could be a spectral Doppler signal recorded in real time or a spectral Doppler signal that was previously recorded and stored in a memory 280. In some embodiments, the Spectral Doppler is buffered so that a portion of the signal that is prior to the trigger can be displayed. For example, the early systole portion of the signal that precedes trigger point 330 as shown in FIG. 6b can be stored in memory and displayed to the operator if desired. In addition, "triggered" and thus time aligned signals can be combined with previously triggered Doppler signals to enhance the signal to noise ratio (SNR). For example, aligned signals could be averaged, or enveloped detected to increase the quality of the signal. Heart beating periods can vary from period to period by about 10% and in order to average or inter-process them, their length can be adjusted by lengthening or shortening signals so that they are the same length prior to averaging or combining them.

In accordance with another embodiment of the disclosed technology, the processor 250 operates to store a consistent number of physiological events in a recorded ultrasound signal instead of predetermined time in seconds as is done in most ultrasound imaging systems today. In one embodiment, the processor is programmed to store Doppler signals that cover a defined number of cycles such as 4, 8 heart beats etc. The processor analyzes the signal as it is being generated for indicators of defined points in the physiological cycle (e.g. peak velocity points) and records the signal until the defined number of points have been detected. For example, in spectral Doppler imaging, the processor may record and store a Doppler signal containing four heart beat events independently of the patient heart rate. In addition, this signal reflecting the predetermined number of heart beats can be shown starting from a desired trigger point as shown in FIG. 6. The processor 250 is programmed to analyze the Doppler signal and determine if a length of Doppler signal includes more or less than the predefined number of physiological events. If fewer than the determined number of physiological events are in the signal, then additional signal is recorded. If a greater number of physiological events are in the signal, then the recorded signal is trimmed to include only the determined number of physiological events. In this way, studies performed on a subject at different times always include the same number of physiological events and are easier to compare. The number of physiological events to be stored may be user defined, may be defined by professional boards, insurance providers or based on common industry practice.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The terms "processor" and "logic circuit" encompass all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit) or hard-wired logic circuitry.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on an imaging system having a display device, e.g., an LCD (liquid crystal display), LED (light emitting diode), or OLED (organic light emitting diode) monitor, for displaying information to the user and a keyboard and a pointing device, e.g., a mouse or a trackball, by which the user can provide input to the computer. In some implementations, a touch screen can be used to display information and to receive input from a user. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. An ultrasound imaging system for performing spectral Doppler imaging, comprising:
    a transducer configured to deliver ultrasound signals into a region of interest of a subject and to detect corresponding echo signals, wherein the ultrasound signals delivered are signals for spectral Doppler imaging interleaved with signals for an other imaging mode;
    a processor coupled to the transducer that is configured to copy a received spectral Doppler signal comprising a first gap and a second gap caused by the other imaging mode; determine first mean frequencies of the received spectral Doppler signal from before the first gap, after the first gap, or before and after the first gap, determine second mean frequencies of the received spectral Doppler signal from before the second gap, after the second gap, or before and after the second gap; determine, using the first mean frequencies, a first portion of a physiological cycle of the subject where the first gap in the received spectral Doppler signal is located, the physiological cycle comprising the first portion and a second portion of the physiological cycle of the subject coupled to the first portion, wherein the second portion of the physiological cycle of the subject where the second gap in the received spectral Doppler signal is located is determined using the second mean frequencies; and adjust one or more signal characteristics of the copied spectral Doppler signal based on the first portion of the physiological cycle of the subject to fill in the first gap, wherein the one or more signal characteristics of the copied spectral Doppler signal is adjusted based on the second portion of the physiological cycle of the subject to fill in the second gap.

2. The ultrasound imaging system of claim 1, wherein the processor is configured to scale a mean frequency of the copied spectral Doppler signal to fill in the first gap based on the first mean frequencies of the received spectral Doppler signal.

3. The ultrasound imaging system of claim 1, wherein the processor is configured to determine the first mean frequencies for portions of the received spectral Doppler signal and to adjust a mean frequency of the copied spectral Doppler signal based on the determined first mean frequencies.

4. The ultrasound imaging system of claim 1, wherein the processor is configured to analyze one or more parameters selected from: a peak frequency, a low frequency, a mean frequency, a median frequency, a variance and a power of the received spectral Doppler signal and to adjust a corresponding parameter of the copied spectral Doppler signal based on the one or more analyzed parameters.

5. The ultrasound imaging system of claim 1, wherein the processor is configured to analyze one or more parameters selected from a peak frequency, a low frequency, a mean frequency, a median frequency, a variance and a power of spectral Doppler signal received before and after the first gap and to adjust a corresponding parameter of the copied spectral Doppler signal such that adjusted parameter lies between the parameter values for the spectral Doppler signal before and after the first gap.

6. The ultrasound imaging system of claim 1, wherein the processor is configured to generate pre-FFT ultrasound data from the copied spectral Doppler signal with the adjusted signal characteristics and to combine the pre-FFT ultrasound data with received pre-FFT data.

7. An ultrasound imaging system for performing spectral Doppler imaging, comprising:
    a transducer configured to deliver ultrasound signals into a region of interest of a subject and to detect corresponding echo signals, wherein the ultrasound signals delivered are signals for a spectral Doppler imaging mode interleaved with signals for an other imaging mode;
    a processor coupled to the transducer that is configured to receive a spectral Doppler signal comprising a first gap and a second gap caused by the other imaging mode; determine first mean frequencies of the received spectral Doppler signal from before the first gap, after the first gap, or before and after the first gap, determine second mean frequencies of the received spectral Doppler signal from before the second gap, after the second gap, or before and after the second gap; determine, using the first mean frequencies, a first portion of a physiological cycle of the subject where the first gap in the received spectral Doppler signal is located, the physiological cycle comprising the first portion and a second portion of the physiological cycle of the subject coupled to the first portion, wherein the second portion of the physiological cycle of the subject where the second gap in the received spectral Doppler signal is located is determined using the second mean frequencies; and adjust driving signals used to interleave the spectral Doppler imaging mode and the other imaging mode so that spectral Doppler imaging is not interleaved with the other imaging mode and the other imaging mode is not used during the first portion and the second portion of the physiological cycle of the subject.

8. The ultrasound imaging system of claim 7, wherein the processor is configured to receive a signal from a sensor that senses a subject's physiological signal and to adjust the driving signals so that the spectral Doppler imaging mode is not interleaved with the other imaging mode during the first portion and the second portion of the physiological cycle based on the subject's physiological signal sensed by the sensor.

9. The ultrasound imaging system of claim 8, wherein the processor is configured to predict a time during which spectral Doppler processing is not to be interleaved with the other imaging mode from the subject's physiological signal sensed by the sensor.

10. The ultrasound imaging system of claim 8, wherein the processor is configured to analyze the subject's physiological signal from the sensor and to predict when a portion of the subject's physiological signal during which the spectral Doppler processing should not be interleaved with the other imaging mode will occur from the analyzed subject's physiological signal.

11. The ultrasound imaging system of claim 7, wherein the processor is configured to adjust a timing of the signals used for the other imaging mode so that the other imaging mode is not used during the time when the spectral Doppler imaging mode is not to be interleaved with the other imaging mode.

12. The ultrasound imaging system of claim 7, wherein the other imaging mode is B-mode processing where ultrasound signals are transmitted along a number of beam lines and the processor is configured to adjust a number of beam lines used during the B-mode such that spectral Doppler processing is not interleaved with the B-mode during the first portion and the second portion of the physiological cycle.

13. The ultrasound imaging system of claim 7, wherein the physiological signal is a cardiac cycle.

14. The ultrasound imaging system of claim 7, wherein the physiological signal is a respiratory cycle.

15. The ultrasound imaging system of claim 7, wherein the processor is configured to receive an input from a user regarding the first portion and the second portion of the physiological cycle during which spectral Doppler processing is not to be interleaved with the other imaging mode.

* * * * *